United States Patent [19]

Kato et al.

[11] Patent Number: 4,677,993

[45] Date of Patent: Jul. 7, 1987

[54] METHOD OF AND APPARATUS FOR INSPECTING CIGARETTE PAPER

[75] Inventors: Yukio Kato; Mikio Komori; Tadao Yonai, all of Tokyo, Japan

[73] Assignee: Japan Tobacco Inc., Japan

[21] Appl. No.: 573,809

[22] Filed: Jan. 25, 1984

[30] Foreign Application Priority Data

Feb. 1, 1983 [JP] Japan .................................. 58-13712

[51] Int. Cl.$^4$ ........................... A24C 5/00; A24C 5/14
[52] U.S. Cl. .................................... 131/280; 131/908; 131/910
[58] Field of Search ........................ 131/280, 908, 910

[56] References Cited

FOREIGN PATENT DOCUMENTS 1479203  7/1977  United Kingdom .

Primary Examiner—V. Millin

Attorney, Agent, or Firm—Brumbaugh, Graves, Donohue & Raymond

[57] ABSTRACT

A method and apparatus for inspecting cigarette paper of eventual cigarette bar unit, which permit further improvement of the precision of inspection, is provided. According to the method and the apparatus, the mean, variance and standard deviation are obtained statistically through a detected pressure signal, then transformation of their normal distribution into a standard normal distribution of $N(0,1)$ where the mean with respect to the probability density function $\Phi(t)$ is 0 and variance with respect to thereto is 1, is obtained. And the estimation of population standard deviation with setting of a significance level is done with the value of t with respect to the probability determined solely by determining the probability in the normal distribution, thereby effecting a decision as to whether the inspected product is non-defective or defective.

11 Claims, 2 Drawing Figures

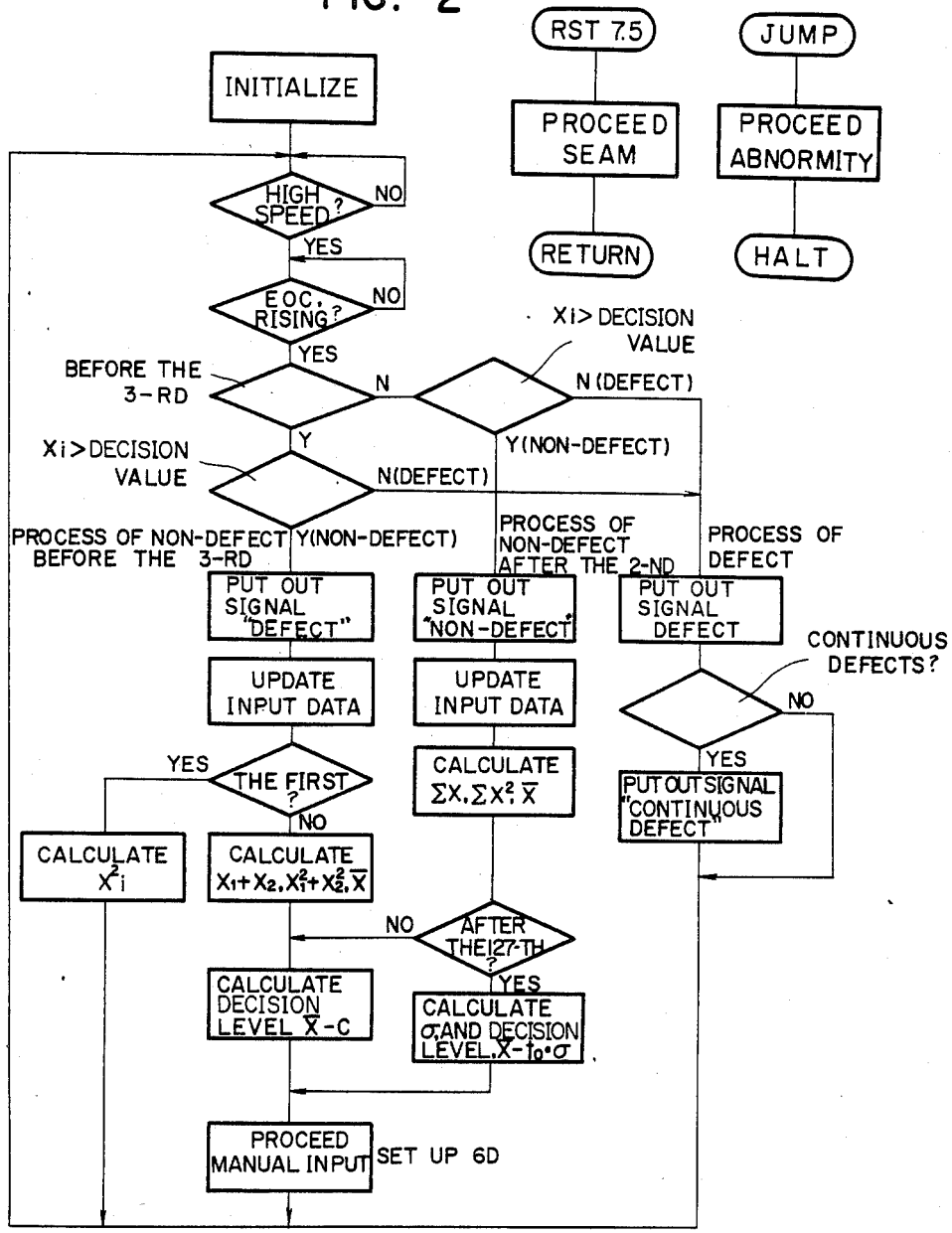

METHOD OF AND APPARATUS FOR INSPECTING CIGARETTE PAPER

BACKGROUND OF THE INVENTION

This invention relates to a method and apparatus for inspecting a quality of cigarette paper of eventual cigarette units making use of air leakage therethrough.

In the manufacture of cigarettes by a cigarette manufacturing machine, defects such as faulty glueing at the time of glueing chip paper which connects a cigarette portion and filter portion and faulty winding at the time of winding of the chip paper which is liable to result in oblique glueing and one-end glueing in addition to the breakage of cigarette paper and pinholes therein can occur. The oblique glueing is a form of faultiness that both edges of the chip paper are glued together not in the circumferential direction but in an oblique direction. The one-end glueing is a faultiness in which one end of the chip paper is not glued in the circumferential direction but remains separated. In either case, a gap is produced between the chip paper and filter, so that an abnormal defective of appearance results.

It is a common characteristics of these faulty products that air leakage results in a defective portion or defective glueing portion when air is forced through the product.

Accordingly, the quality of the product is inspected by supplying air through the product. For example, where the product is a double cigarette, which consists of two eventual cigarettes and a filter sandwiched therebetween with a filter chip paper glued to these components, air is supplied through the double cigarette from one end or both ends thereof, and the air pressure is converted into an electric signal. This air leakage inspection makes use of a phenomenon that the air pressure is reduced by air leakage. The voltage level of the electric signal noted above is compared with a predetermined reference voltage level corresponding to a reference level of air leakage. The inspected double cigarette is inspected to be non-defective or defective depending on the result of the comparison.

Recently, various brands of cigarettes are produced, and it is in practice to use cigarette paper of different air permeabilies suited to the characteristics of various brands in order to provide different characters of quality and different fragrance or aroma features. Generally, the air permeability of cigarette paper varies from not more than 10 ml/min·cm$^2$ of ordinary cigarette paper used for ordinary brands to 24 to 160 ml/min·cm$^2$ of high air permeability kinds of cigarette paper with high density of stoma-like holes used for mild taste of aroma brands. In the case of the high porosity cigarette paper especially, variability of the air permeability occurs in the manufacture in a predetermined range with respect to a nominal air permeability. More specifically, with the same high porosity, the physical properties of cigarette paper, i.e., relative air permeability thereof, varies.

With the conventional apparatus, the detected pressure signal level of low air permeability cigarette paper is high compared to that of high air permeability cigarette paper. This means that even if the detected pressure signal level is reduced to a certain extent due to the detection of a defective product, with the variability of the air permeability thereof being beyond the permissible range, the detected signal level of voltage may be still higher than the reference voltage level. In this case, the double cigarette is deemed to be non-defective (the error of this case being referred to as first kind of error). Conversely, the detected pressure signal level of high air permeability cigarette paper is relatively lower than that of low air permeability cigarette paper. Therefore, it is liable that a sound double cigarette provides a detected pressure signal of lower level than the reference voltage level so that it is deemed to be defective (the error of this case being referred to as second kind of error). The errors as noted will reduce the precision of inspection making it difficult to obtain accurate decision as to whether a double cigarette is non-defective or defective and reducing the quality of the product.

When there occurs a phenomenon of continuously passing defective products or continuously excluding non-defective products in case where high porosity cigarette paper as noted above is used, it has been necessary to adjust a reducing valve while watching a manometer indicating the master pressure of the detected pressure with increasing amount of labour of workers.

In another aspect, a detector used for detecting the pressure usually consists of a pressure-to-electricity conversion element of semiconductor, the detector brings about a thermal drift due to changes in the room temperature caused by heat generation from the machine or other causes. The precision of inspection is reduced by the thermal drift.

In order to solve the problems arising from the variability of the air permeability noted above, it has been proposed to process the detected pressure signal with processing means consisting of averaging means (AGC means) and comparing means as disclosed in Japanese Patent Publication No. 56-46820 and Japanese Patent Preliminary Publication No. 51-82798. Particularly, the early published specification No. 51-82798 discloses an apparatus, in which the detected pressure signal is compensated for by a difference signal between a reference signal obtained in an open to-atmosphere state and detected pressure signal, thereby solving the problems of the thermal drift as well. The apparatuses disclosed in the disclosures noted above, however, basically effects decision only from the standpoint of the mean value, so that the precision of inspection in the population mean estimation is statistically low.

SUMMARY OF THE INVENTION

The present invention seeks to overcome the drawbacks described above in the prior art, and its object is to provide a method and apparatus for inspecting cigarette paper, which permit further improvement of the precision of inspection.

In the method of inspection according to the invention, the mean, variance and standard deviation are obtained statistically through a detected pressure signal, following by transformation of their normal distribution into a standard normal distribution of N (0, 1), in which the mean with respect to the probability density funciton $\Phi(t)$ is 0 and variance with respect thereto is 1. The estimation of population standard deviation with the setting of a significance level is done with the value of t with respect to the probability determined solely by determining the probability in the normal distribution, thereby effecting a decision as to whether the inspected product is nondefective or defective.

More specifically, the air leakage through the cigarette paper (i.e., permeability thereof) is used as a probability variable x, and the population of the whole data with respect to the probability variable x is considered.

With respect to this infinite population, an optional random sample subset of a finite number of air leakage data is considered. The normal distribution P(x) of the air leakage data is given as $$P(x) = \int \frac{1}{\sqrt{2\pi} \cdot \sigma} \cdot e^{-\frac{(x-\bar{x})^2}{2\sigma^2}} dx.$$

where x is the mean of the population, and $\sigma^2$ is the variance thereof.

By setting $$t = (x - \bar{x})/\sigma,$$

the probability density function $\phi(t)$ of the variable t is $$\Phi(t) = \frac{1}{\sqrt{2\pi} \cdot \sigma} \cdot e^{-\frac{t^2}{2}}.$$

Thus, its conversion into a standard normal distribution where the mean is 0 and variance 1 can be obtained. The probability $P(x_1 < x < x_2)$ that there is a certain data x between two arbitrary air leakage data $x_1$ and $x_2$ is given $$P(x_1 < x < x_2) = P(t_1 < t < t_2)$$

$$= \int_{t_1}^{t_2} \Phi(t) dt.$$

where
$$t_i = (x_i - \bar{x})/\sigma \ (i = 1, 2)$$

As a value for determining the level of decision as to whether a product is passed or rejected, an arbitrary constant $t_0$ is set. The probability $P(|x - \bar{x}| < t_0 \cdot \sigma)$ that the air leakage level x is within the range of $\pm t_0 \sigma$ with respect to the mean $\bar{x}$ is $$P(|x - \bar{x}| < t_0 \cdot \sigma) = P(|t| < t_0)$$

$$= 2 \int_0^{t_0} \Phi(t) dt.$$

The value of $t_0$ is thus determined in univalent correspondence the probability $$2 \int_0^{t_0} \Phi(t) dt$$

that the inspected product is passed. The inspected product can be recognized to be non-defective and is thus passed if the air leakage level x satisfies $$|x - \bar{x}| \leq t_0 \cdot \sigma.$$

While it is rejected if the level x satisfies $$|x - \bar{x}| > t_0 \cdot \sigma.$$

The apparatus of inspection for carrying out the method described above according to the invention comprises a pressure-to-electricity conversion element of semiconductor for detecting air leakage, an analog-to-digital converter for converting a detected pressure signal provided as an analog signal into a digital signal, a $t_0$-setter for setting the value of $t_0$ for setting a decision level in the probability density function $\Phi(t)$, and a central processing unit such as a microcomputer for ; excuting operational processing such as estimation of popular standard deviation through mean, variance, standard deviation, and probability density function as to whether the inspected product is passed or rejected, and it is versatile, capable of high speed operational processing and permits highly precise inspection.

BRIEF DESCRIPTION OF THE DRAWINGS

FIG. 2 is a general flow chart for explaining a control program of a central processing unit shown in FIG. 1.

DETAILED DESCRIPTION OF THE EMBODIMENTS

Figure 1:
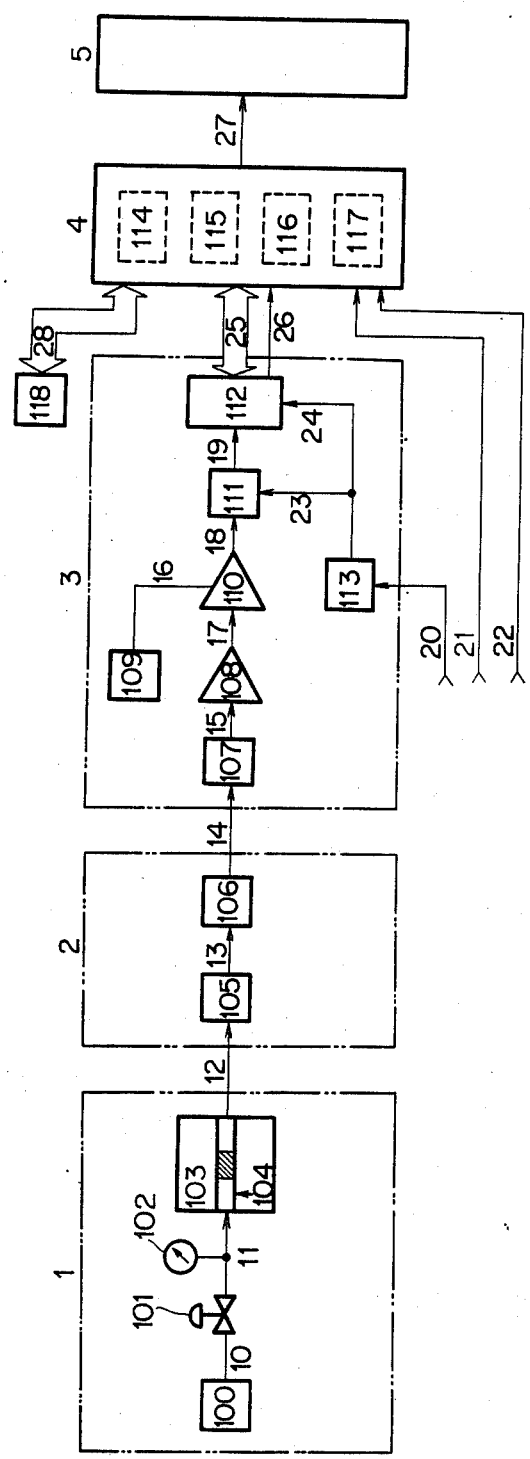
FIG. 1 is a block diagram showing an embodiment of the cigarette paper inspection apparatus according to the invention.

Now, the invention will be described in conjunction with an embodiment thereof illustrated in the drawings.

FIG. 1 shows a block diagram of an apparatus for inspecting cigarette paper according to the invention. Referring to the Figure, reference numeral 1 designates a double cigarette inspection unit. It includes a compressed air source 100, from which air for inspection is supplied through a duct 10. The pressure of the inspection air is adjusted by a reducing valve 101 to a predetermined pressure for the inspection of double cigarettes. The inspection air under the adjusted pressure is led through a duct 11 to be issued against one end of a double cigarette 104, which is held by suction on a continuously rotating inspection drum 103. The adjusted pressure of the inspection air is read out through a pressure gauge 102. The double cigarette 104 has a middle filter portions shown shaded and opposite side cigarette portions.

The inspection air having passed through the double cigarette 104 is led through a lead line 12 to a pressure-electricity conversion unit of semiconductor 2, more particularly a converter 105 having a semiconductor pressure-electricity conversion element in the unit 2. The converter 105 detects the input pressure and converts it into an electric signal as detected pressure signal. If there is air leakage through the cigarette paper, the detected pressure is reduced according to the air leakage, thus reducing the signal voltage level. The detected pressure signal is led through a signal line 13 to a zero adjustment circuit 106. The zero adjustment circuit 106 is provided for zero adjusting of a semiconductor bridge circuit in the semiconductor pressure-electricity converter 105 to produce a highly precise compensated detected signal corresponding detected pressure.

The compensated detected pressure signal is led through a signal line 14 to an analog-to-digital conversion unit 3, more particularly a differential amplifier circuit 107 therein. The differential amplifier circuit 107 will produce a large gain in case of an out-of-phase component of noise to the detected pressure signal while the amplifier circuit 107 produces a small gain in case of an in-phase component of the noise to the signal. This has an effect of reducing the noise level. The differentially amplified output signal is led through a signal line 15 to a high-cut filter 108, the output of which is in turn led through a signal line 17 to an inverting amplifier 110. The gain of the inverting amplifier 110 is set by a gain control circuit 109 which is connected to the inverter/amplifier 110 through a signal line 16.

The invertedly amplified signal output of the inverter/ amplifier 110 is led through a signal line 18 to a sample/ hold circuit 111.

To the sample/hold circuit 111 is supplied a timing signal from a timing signal generator 113 through a signal line 23. The timing signal is generated according to a synchronizing signal, which is produced for every two cigarettes (i.e., every double cigarette) according to the rotation of a rotary section of a cigarette manufacturing machine and supplied to the timing generator 113 through a signal line 20. The sample/hold circuit 111 samples and holds the level of the detected pressure signal as an analog quantity at the instant of applying the timing signal. The analog quantity that is held is fed via a signal line 19 to an analog-to-digital converter 112 to be converted into an 8-bit digital quantity in response to the timing signal noted above which is supplied from the timing generator 113 through a signal line 24. When the analog-to-digital converter 112 has produced the converted 8-bit data, it also produces an end-of-conversion (hereinafter referred to as "EOC") signal indicative of the end of the conversion. The converted 8-bit data and EOC signal are led to a central processing unit 4 through a parallel signal line 25 and a signal line 26, respectively. The central processing unit 4 reads in the converted data in response to the EOC signal.

The central processing unit 4 includes a central processor 114, a read only memory (hereinafter referred to as ROM) 115, a uniform speed random access memory (hereinafter referred to as RAM) 116 and an input/output control unit 117. The central processor 114 performs various operational processes. In the ROM 115, programs for the procedures of the operational processes are stored. In the RAM 116, the read-in data and a series of data including those of mean, variance, standard deviation, etc. are stored. To the central processing unit 4 is connected a t-setter 118, which sets t for decision level setting in probability density function $\Phi(t)$ for the standardization of normal distribution such that the average is 0 and the variance is 1.

Among the procedures for processes stored in the ROM 115 are those for the calculation of the mean, calculation of the variance and standard deviation and decision with respect to a decision level based on the setting of t in the probability density function $\Phi(t)$, these procedures being described later in detail.

The 8-bit detected pressure data noted above, provided from the analog-to-digital converter 112 is temporarily stored in the RAM 116 in synchronism to the timing signal from the timing generator 113. However, since the RAM 116 has a finite storage capacity, it can store only a finite number of data with which to perform calculations. The finite number n of data to be stored can be freely set. This number n is referred to as capacity, and its determination is done as follows.

The sampling frequency $T_0$ of the sample/hold circuit 111 is determined by the rotational speed of the rotary section of cigarette manufactuing machine that operates a synchronization sensor which supplies the synchronizing signal to the timing generator 113. Thus, the time interval of one unit of data collection and storage is the product $T_0 \cdot n$ of the sampling frequency and capacity. Since in this embodiment the unit (i.e., byte) of the central processing unit 4 consists of 8 bits, the value of the capacity n may be an integral multiple of $2^8$ (i.e., 256) or a division thereof by an integral number power of 2. However, the rotational speed of the cigarette manufacturing machine is usually so high that the operational processing must be completed in a period of several milliseconds which corresponds to a processing time for one double cigarette. In this respect, the capacity n is set to $256/2=128$. The time interval $T_0 \cdot n$ noted above is thus of the order of several seconds.

In the meantime, the semiconductor pressure-electricity converter 105 noted above produces a thermal drift depending on the ambient temperature. Generally, the thermal drift is represented by a monotone increasing curve of an upward slope plotted in time units of several ten minutes to several hours after the start of the machine. Thus, it constitutes a DC component in the time interval $T_0 \cdot n$ of the order of several seconds. While the signal component covers a wide frequency region on the high frequence side, the drift component covers only a narrow frequency region of very low frequencies (i.e., on the DC side). For this reason, the thermal drift only slightly varies the average values in statistical operational process, but it has no adverse effects on the variance and standard deviation calculation processes. The slight changes in the average values noted above are very slight and absorbed by the rounding-off error of the least significant digit that is effected in arithmetic operations of one byte to three bytes (i.e., 8 to 24 bits) in the central processing unit 4. Thus, there is no need of making any particular thermal drift compensation either mechanically or electrically.

Since the capacity n is constant, the reading of new sampled data into the RAM 116 necessitates the deletion of one of the previously stored data. This is done by a queuing system or push-up stack system, in which the first stored data is deleted first, that is, by always retroactively storing only the newest n data in the RAM 116.

The data stored in the RAM 116 are used for calculating mean in the central processor 114 following the mean calculation procedure stored in the ROM 115. The sampled data originally stored in the RAM 116 and the calculated mean thus obtained to be stored in the RAM 116 are used for the calculation of the variance and standard deviation in the central processing unit 114 following the variance and standard deviation calculation procedures stored in the ROM 115. The variance and standard deviation values thus obtained are both stored in the RAM 116.

The t-setter 118 consists of a 4-bit input switch and can set $2^4(=16)$ different values of arbitrary t. These values of t correspond to variables of the probability density function $\Phi(t)$ in statistics. The probability that the distance between the measured data and the mean thereof is less than t times the standard deviation is obtained by adding 0.5 to the integral of the probability density function $\Phi(t)$ from o to t. Thus, the probability that the inspected product is passed, corresponds to the integral of the probability density function $\Phi(t)$. This means that once a standard level of air leakage through the cigarette paper corresponding to the passed product is set, the corresponding probability with respect to the passed product is determined in univalent correspondence. The value of t in the probability function $\Phi(t)$ corresponding to the probability of the standard normal distribution fed from the t-setter 118 for setting decision level to the RAM 116 via the signal line 28 is also stored in the RAM 116.

The three values of data, i.e., those of the mean, standard deviation and t in the probability density function Φ(t), stored in the RAM 116, are used for the processing in the central processor 114 for setting the decision level of one-sided test following a population standard deviation estimation procedure stored in the ROM 115. More specifically, when sampled data of the detected pressure signal as measured data is supplied to the central processor 114, which subtracts the mean from the input data, and judges that the pertinent double cigarette is non-defective if the difference between the mean and the input data is less than or equal to the product of the standard deviation and t, while rejecting the double cigarette if the difference is greater than the product. Calculations of the mean variance and standard deviation for the data processing are afresh every time new sampled data is fed, the new data thus obtained being stored afresh in the RAM 116.

When the inspected double cigarette is rejected, an exclusion signal is supplied via the signal line 27 to an exclusion control unit 5.

The central processor 114 receives an operation start signal fed from the machine via a signal line 21, and it starts operational processing after confirming the input of the operation start signal.

In the machine, two paper rolls are set for supplying cigarette paper, and seam is produced between the two paper rolls. Also, the paper of each paper roll has intermediate seams which are produced during the paper making process. Therefore, there are variations of the porosity of high porosity cigarette paper among lots before and after the seams as noted above.

Accordingly a cigarette paper seam signal is supplied from the machine via a signal line 22 to the central processing unit 4, and compensation for the porosity variations of the lots preceding and succeeding a seam is effected by confirming the input of the cigarette paper seam signal and effecting the calculations of the mean, variance and standard deviation afresh by clearing all stored data in response to the cigarette paper sesam signal and obtaining new data.

All the signal lines, along which signals are led to and from the central processing unit 4, are connected to the input/output unit 117, which controls the input and output of signals.

When a finally rejected double cigarette occurs so that an exclusion signal is fed via the signal line 27 to the exclusion control unit 5, the exclusion control unit 5 actuates an exclusion valve. As a result, the rejected double cigarette held by suction on the rotating inspection drum 102 is blown out by compressed air and thus excluded.

The control of the apparatus having the above construction will now be described.

The calculation in the central processing unit 4 with an "operation signal" provided under a normal high speed operating condition of the machine and every time the leading edge of a EOC signal indicative of the end of analog-to-digital conversion is detected, i.e., for every double cigarette. Until the "operation signal" and EOC signal noted above are put in by a programmed input/output system, the central processing unit 4 is in queued state. A "seam interruption" is possible only in this queued state and is impossible while calculation is in force.

The actual content of control is roughly classified into the following three categories. The counting and operational processing are performed only with respect to passed cigarette products.

For the first and second double cigarettes, an "exclusion signal" for excluding the double cigarettes is produced merely when sampled data of the detected pressure signal for each double cigarette is obtained. Since there is no data for comparison at this time, judge is done on data xi with respect to a lower limit level C which is a programmable constant such that the double cigarette is passed if $xi > C$ and rejected if $xi \leq C$.

Next, for the 3-rd to 128-th double cigarettes, the mean $\bar{x}$ of the past data is calculated, and a value $C' = \bar{x} - C$, which is obtained by subtracting a certain constant C from the mean $\bar{x}$, is set as the decision level. The inspected double cigarette is passed if $xi > C'$ and rejected if $xi \leq C'$.

Then, for the 129-th and following double cigarettes, the mean, variance and standard deviation are calculated on the newest 128 pieces of data, and $t_0$ ($t_0$ being a programmable value) times the standard deviation is subtracted from the mean. The resultant value is used as the decision level. The oldest detected pressure signal data is automatically replaced with the newest.

A rejected product, however, is neither counted, nor causes any updating of data.

The control further includes the following functions in addition to the processing described above.

(I) Seam input signal processing function

When a "seam signal" is received the past data can no longer be used, and new calculations are necessary. The seam signal input is used for an interruption, and when the interruption is accepted, the same processing as when the "operation signal" vanishes is performrmed. More specifically, the counter is reset so that the first double cigarette immediately after the seam signal input is dealt with as the first double cigarette, with the first and second double cigarettes being excluded, the comparison of the "mean" and "constant" is executed for the 3-rd to 128-th double cigarettes, and comparison based on the standard deviation being done for the 129-th and following double cigarettes.

(II) Manual input setting function

The decision level can be manually shifted by ±28 (corresponding to ±1.56 V of voltage) at the most at any time even during the operation of the machine from the t-setter 118 which sets t for setting the decision level for fine adjustment of the decision level during operation of the machine. Actually, a value obtained by multiplying a manual input of integer from −7 to +7 by a bias value b (b=0, 0.5, 1, 1.5, 2, 2.5, 3, 3.5, 4) corresponding to the shift amount to the decision level is added to the decision level with no shift.

(III) Continuous reject signal generation function

When n (n being programmable) reject signals are produced continuously from the central processing control unit 4, a "continuous reject signal" is produced. This signal prevails until the "operation signal" is discontinued. The decision as to whether the inspected double cigarette is passed or rejected is done even during the presence of the "continuous reject signal".

(IV) Over variance decision function

When the variance is calculated to be greater than a constant value (which is programmable) continuously for a predetermined number of times (which is programmable), a decision is made that the variance is excessive, that is variations are beyond a controllable range. In this case, the central processing control unit 4 is stopped, and all the double cigarettes are excluded. However, the central processing unit 4 is reset when the power source is disconnected.

FIG. 2 shows a general flow chart of the controls as described above. The individual routines of the processing program will now be described in detail.

(i) Initialization

This routine is executed only once subsequent to the connection of the power source. In this routine, software and hardware are initialized (i.e., inputs and outputs of the input output unit 117 are set, the RAM 116 is cleared, and so forth). Further, the value of $t_0$ involved in the decision level $\bar{x} - t_0 \cdot \sigma$ is determined. The actual setting method will be described after.

(ii) Queued state waiting for input "operation signal"

This routine provides a queued state ready for the execution of program until an "operation signal" is received. No operational processing is performed unless the "operation signal" is issued. Further, after the "operation signal" has been received, a check is done as to whether the "operation signal" is present for every double cigarettes.

(iii) Detection of leading edge of EOC

In this routine, the leading edge of the EOC (end of conversion) signal from the analog-to-digital converter 112 is detected in order to make it possible to fetch stable conversion input data in synchronism to the operation of the machine.

(iv) Input judging

In this routine, proper content of processing is determined according to the input data. More specifically, whether the input data is of a passed or rejected double cigarette is checked, and also a check is done as to whether the passed double cigarette data is of the first or second double cigarette or the data of the third or following one after the issuance of the "operation signal" or a "seam signal".

(v) Processing as passed double cigarette for first and second double cigarettes In this routine, a "reject signal" is issued, and the double cigarettes are excluded. This is done so because the comparison of the input data is done with respect to an absolute level (setting valve $10 \approx 0.39$ V) so that lack of reliability of the decision as to whether the double cigarette is passed or rejected is likely.

For the first double cigarette, only the square root of the input data is calculated, and the decision level is not calculated.

For the second double cigarette, like the case of the 3-rd to 128-th double cigarettes, $\Sigma x = x_1 + x_2$, $\Sigma x^2 = x_1^2 + x_2^2$ and $\bar{x} = \Sigma x/2$ are calculation from data $x_1$ and $x_2$ of the 1-st and 2-nd double cigarettes, and $\bar{x} - C$ (C being a constant value corresponding to the mean) is derived. To this value, a manual shift due to a manual input (which will be described hereinunder) is added to set the decision level for the third double cigarette.

(vi) Processing as passed double cigarette for the 3-rd and following double cigarettes This routine is executed when a decision of the cigarette to be "passed" is done with respect to the previously calculated decision level. In this case, a "non-defect signal" is issued, and also a new decision level for the next decision is calculated.

For the 3-rd to 128-th double cigarettes, $\Sigma x$, $\Sigma x^2$ and $\bar{x}$ are calculated and $\bar{x} - C$ is obtained like the case of the second double cigarette though the number of data used for calculations is different, a shift due to manual input being added to the value thus obtained to provide the decision level for the next decision.

The final decision level is given as $$JL = \bar{x} - C - bD,$$

where b is a bias value between 0 and 4 corresponding to the average, and D is a manually input value of integer from $-7$ to $+7$.

For the double cigarettes after the 127-th one, the values $\Sigma x$, $\Sigma x^2$ and $\bar{x}$ are calculated, and then variance $s' = (\Sigma x^2 - \bar{x}\Sigma x)/128$ and standard deviation $\sigma = C_2\sqrt{s'}(C_2\sqrt{s'} = 1 - \frac{1}{4}n,\ n=128)$ are derived, and $\bar{x} - t_0 \cdot \sigma$ ($t_0$ being a constant) is obtained. Again a shift due to a manual input is added to the value thus obtained to provide the decision level for the next decision.

The final decision level is given as $$JL = \bar{x} - t_0 \cdot \sigma + bD.$$

The values of $\Sigma x$ and $\Sigma x^2$ are calculated for the 3-rd to 128-th double cigarettes by adding the input data to the result of the previous calculation, i.e., using equations $$\sum_{i=1}^{n} x_i = \sum_{i=1}^{n-1} x_i + x_n$$

$$\sum_{i=1}^{n} x_i^2 = \sum_{i=1}^{n-1} x_i^2 + x_n^2$$

For the 129-th and following double cigarettes, the oldest data is subtracted from the result of the previous calculation, and the input data is added to the result, thus obtained equations as follows.

$$\sum_{i=j+1}^{j+128} x_i = \sum_{i=j}^{j+127} x_i - x_j + x_{j+128}$$

$$\sum_{i=j+1}^{j+128} x_i^2 = \sum_{i=j}^{j+127} x_i^2 - x_j^2 + (x_{j+128})^2$$

The calculation of $\sigma$ is done for its different ranges as shown hereinunder using the calculated value of variance $s'$ $$s' = (\Sigma x^2 - \bar{x}\Sigma x)/128$$

in order to improve the speed and precision of calculation of the square root. For the details, refer to the item xi regarding the method of derivation of the standard variation and decision level to be described hereinunder.

(1) For $0 \leq s' \leq 256$, setting $\sigma' = \sqrt{s'}(=\sqrt{256s'}/16)$, $t_0 = 2.3$, the value of $\alpha/64$ ($\alpha$ being constant) is $$2.3 \div \left(1 - \frac{1}{4 \times 128}\right) \times \sqrt{\frac{128}{127}}$$

The shift value $S_F$ is $$S_F = \frac{148}{64} \cdot \sigma' = \sqrt{256s'} \times 1/16 \times 148/64$$

Thus, the shift value $S_F$ is 0 to 37.

(2) For $256 \leq s' \leq 4096$, $\sigma' = \sqrt{16s'}/4$, and the shift value $S_F$ is $$S_F = \frac{148}{64} \cdot \sigma' = \sqrt{16s'} \times 1/4 \times 148/64.$$

Thus, it is 37 to 148.

(3) For $s' \geq 4096$, the variance is excessive, and $S_F$ is at 148.

Theoretically the maximum value $\sigma'$max of $\sigma'$ is 127.5, but the maximum variations are limited by setting $s' \leq 4095$ and $\sigma' \leq 64$ in order to prevent erroneous calculation and comply with the actual control. This is utilized for faultiness processing, i.e abnormity processing to be described later.

(vii) Processing as rejected double cigarette to be defective.

In this routine, the issuance of "defective signal" and increment (+1) to a reject signal counter are effected. When the counter produces a preset counts, i.e., 200 counts, a "continuous defective signal to be defective" is issued. The "continuous defective signal" is reset when the "operation signal" vanishes. As the decision level, the value in the previous decision level is used.

(viii) Seam processing

This routine has such a function that when a "seam signal" is received, the immediately following double cigarette is set as the first one in response to the leading edge of the "EOC signal". Similar process is done as in the case of the "operation signal" vanishing, but the "continuous reject signal" is not discontinued.

(ix) Abnormity processing

This routine is executed when a predetermined number of times of the following cases (1) and (2) occur continuously after proceeding the 129-th and following double cigarette, for instance, in the case of the predetermined time being 100.

(1) For over variance $s' = (\Sigma x^2 - \bar{x}\Sigma x)/ n \geq 4096$, the variance is calculated. (see item (3) of vi) described before) (2) For decision level $(\bar{x} - t_0 \cdot \sigma) \leq$ absolute level (setting value being 0.39). (note; having no component of manual input shift)

This routine is also executed when a runaway program due to a trouble of the central processing unit 4 occurs.

If this routine is executed, "defective signal" and "continuous defective signal" are put out, then the function of the control processing unit 4 will rest. Since this case in different from the case when the "continuous defective signal" occurs, both "defective signal" and "continuous defective signal" are free from resetting even if the "operating signal" vanishes.

(x) Setting decision level

The value of $t_0$ in the decision level $\bar{x} - t_0 \cdot \sigma$ is determined by the state of a 4-bit snap switch for manual input at the time of the closure of the power source. Table 1 shows values of $t_0$ (i.e., set value and actual value) and a constant valve $\alpha$ $$\left(= 64 \, t_o \cdot \frac{1}{1 - \frac{1}{4n}} \cdot \sqrt{\frac{n}{n-1}}, n = 128\right)$$

for individual input data.

The value of $\alpha$ is held once it is set until the power source is disconnected, and it is updated when the power source is connected once again. With the power source connected, the output of the 4-bit switch only serves as manual input for a level shift.

The decision level derived from $\bar{x} - C$ (for $n < 129$) and $\bar{x} - t_0 \cdot \sigma (n \geq 129)$ can be manually shifted through the 4-bit manual input snap switch. Actually, a value obtained by multiplying the input D of integer from $-7$ to $+7$ by the bias value b between 0 and 4, is used as the manual shift value.

TABLE 1

| INPUT | | $t_0$ | | |
|---|---|---|---|---|
| BINARY | DECIMAL | SET VALUE | ACTUAL VALUE | $\alpha$ |
| φφφφ | 0 | 2.30 | 2.299 | 148 |
| φφφ1 | 1 | 1.80 | 1.802 | 116 |
| φφ1φ | 2 | 1.90 | 1.895 | 122 |
| φφ11 | 3 | 1.95 | 1.957 | 126 |
| φ1φφ | 4 | 2.00 | 2.004 | 129 |
| φ1φ1 | 5 | 2.05 | 2.050 | 132 |
| φ11φ | 6 | 2.10 | 2.097 | 135 |
| φ111 | 7 | 2.15 | 2.144 | 138 |
| 1φφφ | 8 | 2.20 | 2.206 | 142 |
| 1φφ1 | 9 | 2.25 | 2.252 | 145 |
| 1φ1φ | 10 | 2.275 | 2.268 | 146 |
| 1φ11 | 11 | 2.325 | 2.330 | 150 |
| 11φφ | 12 | 2.35 | 2.346 | 151 |
| 11φ1 | 13 | 2.375 | 2.377 | 153 |
| 111φ | 14 | 2.40 | 2.408 | 155 |
| 1111 | 15 | 2.45 | 2.454 | 158 |

TABLE 2

| INPUT(D) | | DECISION LEVEL | | | | | | | | |
|---|---|---|---|---|---|---|---|---|---|---|
| | | 0-10 | 11-40 | 41-70 | 71-100 | 101-130 | 131-160 | 161-190 | 191-220 | 221-255 |
| φφφφ | 0 | 0 | 0 | 0 | 0 | 0 | 0 | 0 | 0 | 0 |
| φφφ1 | +1 | 0 | +1 | +1 | +2 | +2 | +3 | +3 | +4 | +4 |
| φφ1φ | +2 | 0 | +1 | +2 | +3 | +4 | +5 | +6 | +7 | +8 |
| φφ11 | +3 | 0 | +2 | +3 | +5 | +6 | +8 | +9 | +11 | +12 |
| φ1φφ | +4 | 0 | +2 | +4 | +6 | +8 | +10 | +12 | +14 | +16 |
| φ1φ1 | +5 | 0 | +3 | +5 | +8 | +10 | +13 | +15 | +18 | +20 |
| φ11φ | +6 | 0 | +3 | +6 | +9 | +12 | +15 | +18 | +21 | +24 |
| φ111 | +7 | 0 | +4 | +7 | +11 | +14 | +18 | +21 | +25 | +28 |
| 111φ | 0 | 0 | 0 | 0 | 0 | 0 | 0 | 0 | 0 | 0 |

TABLE 2-continued

| INPUT(D) | | DECISION LEVEL | | | | | | | |
|---|---|---|---|---|---|---|---|---|---|
| | | 0–10 | 11–40 | 41–70 | 71–100 | 101–130 | 131–160 | 161–190 | 191–220 | 221–255 |
| 1ϕϕ1 | −1 | 0 | −1 | −1 | −2 | −2 | −3 | −3 | −4 | −4 |
| 1ϕ1ϕ | −2 | 0 | −1 | −2 | −3 | −4 | −5 | −6 | −7 | −8 |
| 1ϕ11 | −3 | 0 | −2 | −3 | −5 | −6 | −8 | −9 | −11 | −12 |
| 11ϕϕ | −4 | 0 | −2 | −4 | −6 | −8 | −10 | −12 | −14 | −16 |
| 11ϕ1 | −5 | 0 | −3 | −5 | −8 | −10 | −13 | −15 | −18 | −20 |
| 111ϕ | −6 | 0 | −3 | −6 | −9 | −12 | −15 | −18 | −21 | −24 |
| 1111 | −7 | 0 | −4 | −7 | −11 | −14 | −18 | −21 | −25 | −28 |
| (b) | | ×0 | ×0.5 | ×1.0 | ×1.5 | ×2.0 | ×2.5 | ×3.0 | ×3.5 | ×4.0 |

Table 2 shows manual shift values corresponding to individual input values D and decision levels.

For example, when the decision level is to be set to $\bar{x}-2.3\sigma+0b$, the switch may be set to "0000" (i.e., all bit "off") both before and after the connection of the power source.

When the decision level is to be set to $\bar{x}-2.2\sigma+3b$, the switch may be set to "1000" before the connection of the power source and "0011" after the connection.

The shift value that is manually input can be freely varied at any time after the connection of the power source.

(xi) When estimating the parameter from the statistical values of the decision level (rejection values), the population mean $\mu$, population variance $S=\sigma^2$ and population standard deviation $\sigma$ are generally expressed as $$\bar{x} \rightarrow \mu$$

$$V = \frac{\Sigma(x-\bar{x})^2}{n-1} \rightarrow S$$

$$\frac{\sqrt{V}}{C_2^*} = \frac{1}{C_2^*}\sqrt{\frac{\Sigma(x-\bar{x})^2}{n-1}} \rightarrow \sigma$$

where $$C_2^* = 1 - 1/4n \quad (n \geq 20).$$

Where the rejection region is set to $t\cdot\sigma$, the shift value $S_F$ and rejection value $R_F$ from the mean values are given as $$S_F = t_0 \cdot \sigma$$

$$= t_0 \cdot \left(\frac{1}{1-\frac{1}{4n}}\right) \cdot \sqrt{\frac{\Sigma(x-\bar{x})^2}{n-1}}$$

$$R_E = \bar{x} - t_0 \cdot \sigma$$

For simplifying the calculations and increasing the speed of operation of the microcomputer, the above equations are transformed into $$S_F = t_0 \cdot \left(\frac{1}{1-\frac{1}{4n}}\right) \cdot \sqrt{\frac{\Sigma x^2 - 2\Sigma x \cdot \bar{x} + n\bar{x}^2}{n-1}}$$

$$= t_0 \cdot \left(\frac{1}{1-\frac{1}{4n}}\right) \cdot \sqrt{\frac{\Sigma x^2 - \bar{x}\Sigma x}{n-1}}$$

-continued $$= t_0 \cdot \left(\frac{1}{1-\frac{1}{4n}}\right) \cdot \sqrt{\frac{n}{n-1}} \cdot \sqrt{\frac{\Sigma x^2 - \bar{x}\Sigma x}{n}}$$

By setting $$\frac{\alpha}{64} = t_0 \cdot \left(\frac{1}{1-\frac{1}{4n}}\right) \cdot \sqrt{\frac{n}{n-1}} \quad (\alpha \text{ is a constant})$$

then, $S_F$ is as follows;

$$S_F = \frac{\alpha}{64} \cdot \sqrt{\frac{\Sigma x^2 - \bar{x}\Sigma x}{n}}$$

Where the number of data n is; n=128, $t_0$ is; $t_0=2.3$ and the input data xi is an 8-bit digital input, the maximum value $S_F(\max)$ of $S_F$ theoretically occurs when the variation is maximum, i.e., xi=255×64, 0×64 ($\bar{x}=255\times64/128=127.5$). At this time, $$S_F(\max) = 2.3 \times 1/(1 - 1/[4 \times 128]) \times \sqrt{128/127} \times$$

$$\sqrt{(4161600 - 127.5 \times 16320)/128} \approx 294.98.$$

Also, $R_E$ is $$R_E = \bar{x} - S_F(\max) = 127.50 - 294.98 = -167.48.$$

This is meaningless, that is, this means that all double cigarettes are passed. Actually, therefore, correction is made such that the upper limit of $S_F$ is 148 (which corresponds to a voltage level of 5.781 V) and $R_E$ will not be less than a certain preset value.

(xii) Updating of input data

It is only when the input data xi (i=1, 2, ..., 128) is of a passed double cigarette that the old data is updated by new data. This is done by storing the data xi in the i-th one of storage areas (with addresses of DATA to DATA +127) of the RAM 116. The storage areas are cleared to "0" at the time of the initialization, but they are not cleared when the normal high speed operation is resumed after it has been temporarily interrupted. That is, it is cleared only at the time of the connection of the power source.

In the above embodiment of the cigarette paper inspection apparatus, a microcomputer is used to effect data processing digitally. However, it is also possible to construct the apparatus for carrying out the method according to the invention without using any microcomputer but using an analog operational circuit.

The apparatus using a microcomputer as in the above embodiment, however, although it is slightly inferior to an equivalent analog circuit in the processing speed, etc., is advantageous in many aspects such as freedom from noise, reliability of data processing at the time of the rising of high speed operation and at the time of a seam detection, precision of signal processing and operational processing, readiness of adjustment and service and readiness of handling data of rejected products.

As has been described, the mean, standard variance, etc. are statistically calculated according to data, and decision as to whether an inspected product is passed or rejected is done by using the results of calculations and predetermined constants in the probability density function distribution, so that very high precision of inspection can be obtained.

Further, the signal having the temperature drift occured in the semiconductor pressure-to-electricity conversion element is compensated for in the stage of the statistical operational processing and there is no need of providing any separate temperature drift compensation means, which is desired from the standpoint of cost.

Further, the predetermined constants noted above can be freely set to provide for a specific standard deviation for each brand. It is thus possible to set optimum reference for the rejected and passed product exclusion factors for each brand, thus permitting improvement of the product quality and reduction of the cost of manufacture.

What is claimed is:

1. A method of inspecting cigarette paper of eventual cigarette bar comprising the steps of
    (a) detecting a pressure varying with air leakage through cigarette paper of an eventual cigarette bar;
    (b) converting said detected pressure into a corresponding electric signal;
    (c) transforming said electric signal into digital data;
    (d) storing said digital data;
    (e) calculating mean, variance and standard deviation from said stored digital data for each eventual cigarette bar;
    (f) obtaining a decision level by substracting a product of a predetermined constant and standard deviation from said mean; and
    (g) making a decision as to pass the inspected eventual cigarette bar when said data thereof is higher than said decision level and as to reject the cigarette bar when said data thereof is lower than the decision level.

2. A method of inspecting cigarette paper according to claim 1, wherein said steps are performed by routines of the processing program.

3. A method of inspecting cigarette paper according to claim 2, wherein said routines having steps of
    (a) initializing all old data;
    (b) queueing state for waiting input operational signal;
    (c) detecting of leading edge of end of conversion signal;
    (d) judging input;
    (e) processing as passed double cigarette for first and second double cigarette;
    (f) processing as passed double cigarette for third and following double cigarettes;
    (g) processing as rejected double cigarette to be defective;
    (h) seam processing;
    (i) abnormity processing;
    (j) setting decision level;
    (k) estimating the parameter from the statistical values of the decision level and calculating the population mean, population variance and population standard deviation;
    (l) calculating a shift value and rejecting value; and
    (m) updating of input data.

4. A method of inspecting cigarette paper according to claim 3, wherein said steps (a) to (m) are repeated.

5. A method of inspecting cigarette paper according to claim 4, wherein said repeated steps (a) to (m) perform seam input signal processing function, manual input setting function, continuous reject signal generation function and over variance decision function.

6. An apparatus for inspecting a cigarette paper of eventual cigarette bar comprising
    a double cigarette inspection unit for detecting a pressure varying with air leakage through cigarette paper of an eventual cigarette bar;
    a pressure-to-electricity conversion element for converting said detected pressure into a corresponding electric signal;
    analog-to-digital conversion means for transforming said electric signal into digital data through sampling;
    central processing control means having
    (1) read only memory means storing an operational processing program for obtaining mean, variance and standard deviation from the digital data obtained from said conversion means and for also obtaining a decision level according to said mean and standard deviation and predetermined constants, and storing a procedure program for a decision processing for making a decision as to whether the inspected eventual cigarette bar and said decision level,
    (2) uniform speed random access memory means for storing said digital data and also the mean, variance standard deviation and population standard deviation data, and
    (3) central processing means for executing operational processing and decision processing following the program procedure stored in said read only memory means; and
    setting means for setting constants for setting said decision level.

7. An apparatus for inspecting a cigarette paper of eventual cigarette bar according to claim 6, wherein said pressure-to-electricity conversion element is a semiconductor element.

8. An apparatus for inspecting a cigarette paper of eventual cigarette bar according to claim 6, wherein said setting means is a snap switch for setting input manually according to a condition, said condition being concerned decision level and connection to the power source.

9. An apparatus for inspecting a cigarette paper of eventual cigarette bar according to claim 6, wherein said analog-to-digital convertion means is synchronously controlled through a timing generator.

10. An apparatus for inspecting a cigarette paper of eventual cigarette bar according to claim 9, wherein said timing generator is connected to receive a synchronization signal from a synchronization sensor for controlling said analog-to-digital conversion means and a sample/hold circuit, said sample/hold circuit being connected to the analog-to-digital conversion means.

11. An apparatus for inspecting a cigarette paper of eventual cigarette bar according to claim 6 and 10, wherein, said synchronization sensor is operated by a rotary section of said double cigarette inspection unit.

* * * * *

UNITED STATES PATENT AND TRADEMARK OFFICE
CERTIFICATE OF CORRECTION

PATENT NO. : 4,677,993

DATED : July 7, 1987

INVENTOR(S) : Kato et al.

It is certified that error appears in the above-identified patent and that said Letters Patent is hereby corrected as shown below:

Column 2, line 15, "porositity" should read --porosity--;
Column 2, lines 57-58, "funciton" should read --function--;
Column 3, line 39, "$\pm t_0 \sigma$" should read --$\pm t_o . \sigma$--;
Column 4, line 5, "excuting" should read --executing--;
Column 7, line 39, "sesam" should read --seam--;
Column 8, line 32, "perforrmed" should read --performed--;
Column 10, line 12, "JL=x-C-bD" should read --JL = $\bar{x}$ - C + bD--;
Column 11, line 12, that portion of the equation reading "$\leq$" (2nd occurrence) should read --<--;
Column 11, line 20, "$S_F$ is" should read --$S_F$ is fixed--;
Column 12, line 9, "in" should read --is--;

Column 16, lines 32-34, "for making a decision as to whether the inspected eventual cigarette bar and said decision level," should read --for making a decision as to whether the inspected eventual cigarette is passed or rejected and said decision level--
Column 16, line 56, "convertion" should read --conversion--.

Signed and Sealed this

Twelfth Day of April, 1988

Attest:

DONALD J. QUIGG

Attesting Officer

Commissioner of Patents and Trademarks